United States Patent
Overmyer et al.

(10) Patent No.: US 10,849,999 B2
(45) Date of Patent: Dec. 1, 2020

(54) METHOD FOR DISINFECTING PRESSURIZED ASSISTED BREATHING MACHINES AND MAINTAINING SAID MACHINE'S AIR QUALITY

(71) Applicants: Thad J. Overmyer, Danville, KY (US); Michael Overmyer, Danville, KY (US)

(72) Inventors: Thad J. Overmyer, Danville, KY (US); Michael Overmyer, Danville, KY (US)

(73) Assignees: Michael Overmyer, Danville, KY (US); Thad J. Overmyer, Danville, KY (US)

( * ) Notice: Subject to any disclaimer, the term of this patent is extended or adjusted under 35 U.S.C. 154(b) by 0 days.

(21) Appl. No.: 16/878,548

(22) Filed: May 19, 2020

(65) Prior Publication Data

US 2020/0276343 A1    Sep. 3, 2020

Related U.S. Application Data

(63) Continuation-in-part of application No. 15/793,618, filed on Oct. 25, 2017, now Pat. No. 10,785,998.

(51) Int. Cl.

| | |
|---|---|
| *A61M 16/06* | (2006.01) |
| *B08B 9/032* | (2006.01) |
| *A61L 2/18* | (2006.01) |
| *A61M 16/00* | (2006.01) |
| *A61M 16/10* | (2006.01) |

(52) U.S. Cl.
CPC ............ *A61L 2/18* (2013.01); *A61M 16/0057* (2013.01); *A61M 16/06* (2013.01); *A61M 16/105* (2013.01); *B08B 9/0321* (2013.01); *A61L 2202/17* (2013.01); *A61L 2202/24* (2013.01); *A61M 2209/10* (2013.01); *B08B 2209/032* (2013.01)

(58) Field of Classification Search
CPC ....................................................... A61L 2/18
USPC ............... 422/1, 28; 134/22.11, 22.14, 22.19
See application file for complete search history.

(56) References Cited

U.S. PATENT DOCUMENTS

| | | | | |
|---|---|---|---|---|
| 5,424,323 | A * | 6/1995 | Wachman | A01N 59/00 514/247 |
| 6,475,434 | B1 * | 11/2002 | Darouiche | A61L 2/0082 422/28 |
| 7,329,412 | B2 * | 2/2008 | Modak | A61K 31/155 424/423 |
| 8,381,345 | B2 * | 2/2013 | Vazales | A61M 16/0434 15/104.05 |
| 9,622,481 | B2 * | 4/2017 | Gawande | A01N 47/44 |
| 9,623,452 | B2 * | 4/2017 | Przyjemski | B08B 9/0321 |
| 9,884,349 | B2 * | 2/2018 | Falk | B08B 3/02 |
| 10,016,575 | B2 * | 7/2018 | Vazales | A61M 25/00 |
| 10,412,968 | B2 * | 9/2019 | Alimi | A61L 2/18 |
| 10,785,998 | B2 * | 9/2020 | Overmyer | C07C 279/265 |
| 2010/0175721 | A1 * | 7/2010 | Eli | A61M 16/0666 134/22.11 |
| 2016/0095876 | A1 * | 4/2016 | Salamone | A61K 8/9789 424/43 |
| 2018/0280582 | A1 * | 10/2018 | Grossman | A61L 31/08 |

* cited by examiner

*Primary Examiner* — Nina Bhat
(74) *Attorney, Agent, or Firm* — Michael Overmyer; Thad J. Overmyer

(57) ABSTRACT

A method for disinfecting a contaminated pressurized assisted breathing machine, namely a sleep apnea machine including said machine's components and maintaining said machine's fluid quality between use on patients, which comprises the steps of preparing an aqueous solution comprising alcohol-glycerin-chlorhexidine gluconate-dye-flavoring agent; purging and removing machine's existing fluid from said machine and said machine's components; introducing the said aqueous solution into said machine and said machine's components; purging with pressurized fluid by removing said aqueous solution and contaminants from said machine and said machine's components; introducing pressurized fluid into said machine and said machine's components for flushing and rinsing said machine and said machine's components.

3 Claims, No Drawings

METHOD FOR DISINFECTING PRESSURIZED ASSISTED BREATHING MACHINES AND MAINTAINING SAID MACHINE'S AIR QUALITY

CROSS REFERENCE TO RELATED APPLICATION

This application is a continuation-in-part of my co-pending application of the title, "A single composition comprising a disinfectant and a lubricant combined with a method of using said composition comprising to disinfect and/or lubricate a fluid encompassing system" filed Oct. 25, 2017 and given Ser. No. 15/793,618.

BACKGROUND OF THE INVENTION

A fluid encompassing system that dispenses a fluid or fluids for in vitro and/or in vivo procedures and/or for consumption must be disinfected.

The present invention provides a method to disinfect a contaminated system, namely a system that is a pressurized assisted breathing machine that supplies air to a patient. Air is the fluid that is encompassed in this machine and dispenses air from this machine to the patient. This method helps maintain said machine's air quality by disinfecting the environment in which said machine's air contacts. Examples of an assisted breathing machine herein referred to in this invention comprise of mechanical ventilation machines, a ventilator, manual hand-operated bag valve mask, resuscitators, respirators, and sleep apnea machines.

Bacteria exposure, mold exposure, foul odor, increased risk for sinus infections and pneumonia, allergy symptoms, mineralization within machine and premature machine breakdown are some of the risks that occur if an assisted breathing machine is not disinfected properly. After the use of this machine, bacterial contaminants remaining in this machine creates contamination within the machine and also contaminates the air that is dispensed and encompassed in this machine.

Disinfecting an assisted breathing machine routinely will help maintain and control the air quality for the air that is encompassed and dispensed from this assisted breathing machine.

Mechanical ventilation machines are assisted breathing machines that supply air to a patient. There are two main types of mechanical ventilation machines: negative pressure machines and positive airway pressure machines. A positive airway pressure machine pumps air under pressure into the airway of the patient's lungs. Negative pressure machine is when air is sucked into the lungs by stimulating movement of the chest.

A common treatment prescribed for patients suffering from the symptoms of Obstructive Sleep Apnea is the use of a Continuous Positive Airway Pressure sleep apnea therapy machine. This sleep apnea machine comes in three forms: CPAP (Continuous Positive Airway Pressure), BiPAP (Bi-level Positive Airway Pressure) and APAP (Automatic Positive Airway Pressure). Though these three types of sleep apnea machines differ in the air pressure that machine maintains during therapy, all three machines have the same components: a sleep apnea machine reservoir, sleep apnea machine tubing, sleep apnea machine breathing mask, and sleep apnea machine air filter aimed to provide a gentle flow of pressurized and filtered air that aids in sleep.

These machines become contaminated and must be disinfected prior to use. Disinfecting these machines routinely will help maintain and control this machine's air quality. When this machine is not disinfected properly, bacterial contaminants remaining in this machine will create biofilm, which contaminates this machine's encompassing fluid, air and said machine.

Biofilm is a build up of a slimy layer of bacteria that adheres to the surfaces of said machine that encompass a fluid. Although many bacteria can grow in a free-living, planktonic state, it is quite common for them to adhere to surfaces by producing extra-cellular polysaccharide or in some cases by means of specialized structures termed holdfasts. The adherent bacteria produce micro-colonies, leading to the development of biofilm, which initially may be composed of only one bacterial type, but frequently develop to contain several bacteria living in a complex community. In fact, every surface exposed to fluids and/or nutrients will become colonized by microorganisms. This formation of bacteria may be harmful and can result to fatality.

A pressurized assisted breathing machine, namely sleep apnea machines are both susceptible to biofilm. During the use of this machine, a buildup of contaminants, including bacteria, forms within said machine's components. These contaminated components bacterially penetrate this machine's encompassing fluid, air. Biofilm affects the machine's air quality. When said dispensing air becomes bacterial compromised, the properties of said air are altered.

The inner walls of said machines' components are the location of the biofilm and microbial contamination. Free-floating microbes initially adhere to the inner walls of said components and form a bacterial layer. This microbial layer becomes a growing mass of bacteria. Some bacteria become planktonic and migrate elsewhere in said machine's components.

The build-up of microbial contamination and biofilm in a sleep apnea machine can provide mold exposure, bacteria exposure, allergy symptoms, increased risk for sinus infections and pneumonia to the patient especially immunosuppressed patients. This biofilm buildup within said machine can likely can cause premature machine breakdown, mineralization within said machine and foul tastes and odors in said machine and said machine's air.

Various types of disinfectants are recommended to disinfect said machine. When a disinfectant is not completely removed from this machine, the chemical and physical properties of this machine's air are affected from the remnants of the disinfectant and contamination from said machine.

Microbial contamination and biofilm inside the sleep apnea machine affects said machine's air quality. When said machine's air becomes bacterial penetrated by the contaminated sleep apnea machine and said machine's components, this machine's air composition and air quality are altered.

A combination of any of the following encourages rapid growth of microorganisms in the sleep apnea machine: stagnant water in the reservoir, warm water temperatures in the reservoir, poor hygienic ethics by patient, contaminated breathing mask, contaminated sleep apnea machine tubing, contaminated sleep apnea machine filter, contaminated sleep apnea machine reservoir, and water source.

All water sources used for the sleep apnea machine are susceptible to biofilm. Water without an antimicrobial agent will become more contaminated than water treated with an antimicrobial agent. The common water sources are municipal water, distilled water, spring bottled water, and well water.

The municipal drinking water source is treated with chlorine, an antimicrobial agent, to ensure this water is a safe drinking water for the community. However, not all cities have quality drinking water. Depending on the geographic area, some cities may have hard municipal water.

When patients use hard municipal water for their sleep apnea machine water, the hard water mineral deposits: calcium, magnesium, and iron contribute to biofilm growth in the sleep apnea machine. These mineral deposits from the hard municipal water can also impact the life span of the sleep apnea machine; however, the present invention's method are not affected by a patient's water source for their sleep apnea machine.

Distilled water source and spring bottled water source have a 24-hour shelf life once opened, since they do not contain an antimicrobial agent.

Sleep apnea machine patients that live in the rural areas that use well water as their water source for their sleep apnea machine do not contain any antimicrobial agents.

All water sources including treated water are susceptible to biofilm. Examples of treated water: municipal water, filtered water, UV treated water, purified water, spring bottled water, and distilled water.

The water treatment products do not disinfect sleep apnea machine.

Water treatment products only treat to purify the water. Water treatment products and treated water do not remove biofilm from the sleep apnea machine.

For example, treated water is supplied to contaminated sleep apnea machine. This treated water becomes bacterially penetrated and contaminated when contacting the contaminated sleep apnea machine and machine's components, which results with the sleep apnea machine having contaminated air for the patient.

This invention's method disinfects said machine and machine's components in order to maintain and control the sleep apnea machine's air quality by cleaning the microbial contamination and biofilm from the sleep apnea machine and machine's components.

The present invention's intermittent disinfectant treatment is used in between patient's use of said sleep apnea machine. The present's invention's intermittent disinfectant treatment results with a flush/rinse of said machine that does not result in patient exposure to said disinfectant composition, microbial contamination and biofilm when this invention's method is performed.

SUMMARY OF THE INVENTION

Pressurized assisted breathing machines, namely sleep apnea machines must be disinfected after each use, because the patients are susceptible to microbial contamination and biofilm growth, which can likely cause illness to the patient. This invention's method using this composition performed routinely disinfects and controls the microbial contamination and biofilm in this machine, which ensures this machine's air is not contaminated.

This present invention provides a method maintaining a pressurized sleep apnea machine's air quality between use on patients, wherein said sleep apnea machine's components includes a sleep apnea machine reservoir, sleep apnea machine tubing, sleep apnea machine breathing mask, sleep apnea machine air filter, comprising the steps of preparing an aqueous solution comprising 5-35% by volume of alcohol, 10-50% by volume of glycerin, 0.06-2% by volume of chlorhexidine gluconate, dye and flavoring agent; purging and removing water from said sleep apnea machine and said machine's components; introducing the said aqueous solution into said sleep apnea machine and said machine's components; purging and removing said aqueous solution and contaminants from said sleep apnea machine and said machine's components; introducing water into said sleep apnea machine and said machine's components for flushing and rinsing said machine and said machine's components.

This invention's method disinfectant's ingredients are water-soluble that does not leave residue and does not create corrosion within said machine and said machine's components.

The importance of this invention's method combined with this invention's disinfectant composition are utilized together routinely helps disinfect and control the microbial contamination and biofilm within this machine and components, which helps maintain said machine's air quality.

DESCRIPTION OF THE PREFERRED EMBODIMENT

This invention's disinfecting method for pressurized assisted breathing machines, namely sleep apnea machines helps maintain said machine's air quality, the functioning of machine and protect the health of said machine's user, the patient.

This invention's disinfectant composition is an aqueous solution comprising 5-35% by volume of alcohol, 10-50% by volume of glycerin, 0.06-2% by volume of chlorhexidine gluconate, dye and flavoring agent.

This composition's ingredient, alcohol, is a denatured ethanol, which comprises denaturants. This composition's denaturants are flavoring agents that indicate when this invention's method using said disinfectant composition is performed incorrectly.

This composition's ingredient, chlorhexidine gluconate, is a disinfectant and is commercially available in liquid form as chlorhexidine.

This composition's ingredient, glycerin, is a trihydric alcohol and a humectant.

This composition's ingredients glycerin and the alcohol denaturants help masks the foul odors that are caused by this contaminated fluid encompassing system.

This composition's ingredients: chlorhexidine gluconate and alcohol (glycerin, a trihydric alcohol, and the ethanol alcohol) are preservatives for this composition.

This composition's percentage volumes of the glycerin (trihydric alcohol), and chlorhexidine gluconate are this composition's disinfectant ingredients when formulated together. This method using this composition creates both a physical and chemical reaction on the microbial contamination and biofilm in this sleep apnea machine and said machine's components.

A physical reaction occurs when this method using said composition's disinfectant ingredient, glycerin, also a humectant, attracts water from within the biofilm cell structure causing a change in the physical properties.

A chemical reaction occurs when this method using said composition's disinfectant ingredient, chlorhexidine gluconate, alters the biofilm.

This composition may include a dye, a cosmetic ingredient or a coloring agent. This composition's dye serves as an indictor to show a different color from said machine's encompassing fluid.

The present invention provides a method using this invention's disinfectant composition comprising of purging said machine and said machine's components, adding said disinfectant composition into empty said machine, and flushing/rinsing said machine. This method ensures that this composition is not diluted and that this composition directly contacts the microbial contamination and biofilm in this machine.

This contaminated sleep apnea machine and said machine's components will bacterially penetrate and contaminate this machine's air quality. Disinfecting this machine and said components routinely with this invention's method will maintain and control physical and chemical properties of this machine's air.

This method's first step, purging sleep apnea machine, removes said machine's encompassing fluid by a gravity-fed system; and/or a pressurized gas; and/or purging with pressurized gas combined with vacuum suction.

This method's second step, adding this invention's composition into said machine's empty components ensures this disinfectant composition is not diluted and that this composition directly contacts the microbial contamination and biofilm in this machine. This composition remains in the machine for a period of time to have an effect upon the microbial contamination and biofilm. Furthermore, this composition will remain in said machine and components when this machine is not being utilized comprising of consecutive days until this machine is ready to be utilized again.

After this period of time of disinfecting this machine and said components is complete, this method's final step, flushing/rinsing said machine adds a fluid into said machine's components. Water may be used as a fluid to flush/rinse said machine and said machine's components; and/or flushing/rinsing said machine is achieved by using a pressurized gas; and/or this method of flushing/rinsing said machine is achieved by a gravity-fed system.

After this invention's method is completed using said disinfectant composition comprising this composition's ingredients, glycerin and the denaturants from the denatured ethanol, help masks the foul odors that are caused by the microbial contamination and biofilm in said contaminated machine and said components.

This invention's disinfectant composition adheres to the inner walls of the sleep apnea machine tubing and sleep apnea mask surface to prevent buildup of contamination. This invention's disinfectant composition breaks down the layers of contamination that is attached to the inner walls of the sleep apnea machine tubing and mask. This invention's disinfectant composition cleans the contaminated surfaces of the sleep apnea machine's water reservoir and cleans the sleep apnea machine's air filter by immersion. Permeated cloth with invention's disinfectant composition stuffed inside the mask to prevent dust and other debris buildup from entering the tubing when not in use.

The invention's preferred method describes in greater detail when cleaning the sleep apnea machine's components. The machine should be unplugged from the electrical power source. The machine's components include the sleep apnea machine tubing, sleep apnea machine mask, sleep apnea machine reservoir, and sleep apnea machine filter should be placed on a dry flat surface near a sink. Leave the sleep apnea machine at its operational site. Step 1: Remove sleep apnea machine's water reservoir and disconnect sleep apnea machine's tubing. Step 2: Dispose water from the sleep apnea's reservoir and empty into nearby sink. Step 3: Disassemble reservoir: Remove reservoir's top and reservoir's inner platform in order to have access to the reservoir's base. Step 4: Saturate clean cloth with invention's disinfectant and wipe the inner walls of the empty reservoir, inside of the reservoir's top, and both sides of the reservoir's platform. STEP 5: Re-saturate cloth with said disinfectant and wipe the sleep apnea machine's breathing mask internally and externally. Step 6: Place mask inside empty reservoir. Step 7: Pour said invention's disinfectant inside said mask. Step 8: Take the end of the tubing that was connected to the sleep apnea machine and now plug that tubing opening with a rubber plunge stopper. Step 9: Take the other end of the tubing and pour the invention's disinfectant into this tubing's opening. After invention's disinfect is poured then plug that tubing's opening with the other rubber plunge stopper. Step 10: Each hand should hold an end of the sleep apnea machine tubing. Move each hand up and down 3 times so the invention's disinfectant coats the entire inside of the tubing's inner walls. This is accomplished by lowering one of the tubing and raising the other end of the tubing. Alternating this movement moves the invention's disinfectant through the tubing. Step 11: After completing this coating, place the tubing on a flat surface. Allow the invention's disinfectant to stay inside the tubing over the next 8 hours. Step 12: Place the sleep apnea machine air filter inside the reservoir. Saturate the filter with the invention's disinfectant. Immediately squeeze dry the air filter and place the air filter on a clean absorbent cloth and dry flat surface. Step 13: After eight hours, remove the rubber plunge stopper from the end of the tubing that connects to the sleep apnea machine. Raise the tube's opening and drain the invention's disinfectant into a nearby sink. Step 14: Flush and Rinse the tubing with water from preferred water source. Step 15: Assemble the sleep apnea machine components back together. Step 16: Fill the sleep apnea machine reservoir with preferred water and turn ON the machine. Turn machine OFF if you hear gurgling noise in the tubing then drain the tubing or disassemble the mask. Turn ON the machine. Place the machine on a countertop, have the mask end of the tubing in a lower position and then allow the air to push any remaining water from the tubing.

What is claim is:

1. A method for disinfecting a contaminated pressurized assisted breathing machine including said machine components and maintaining said machine fluid quality between use on patients, comprising the steps of:
    a) preparing an aqueous solution comprising 5-35% by volume of alcohol, 10-50% by volume of glycerin, 0.06-2% by volume of chlorhexidine gluconate, dye and flavoring agent;
    b) purging with pressurized fluid by removing fluid from said machine and said machine components;
    c) introducing the aqueous solution of step a) into said purged machine and said purged machine components;
    d) purging and removing said aqueous solution and contaminants from said machine and said machine components with pressurized fluid;
    e) introducing pressurized fluid into said machine and said machine components for flushing and rinsing said machine and said machine components.

2. A method for maintaining a pressurized sleep apnea machine air quality between use on patients, wherein said sleep apnea machine components includes a sleep apnea machine reservoir, sleep apnea machine tubing, sleep apnea machine breathing mask, sleep apnea machine air filter comprising the steps of:
    a) preparing an aqueous solution comprising 5-35% by volume of alcohol, 10-50% by volume of glycerin, 0.06-2% by volume of chlorhexidine gluconate, dye and flavoring agent;
    b) purging and removing water from said sleep apnea machine and said machine components;

c) introducing the aqueous solution of step a) into said sleep apnea machine and said machine components;

d) purging and removing said aqueous solution and contaminants from said sleep apnea machine and said machine components;

e) introducing water into said sleep apnea machine and said machine components for flushing and rinsing said machine and said machine components.

3. A method for disinfecting a contaminated pressurized sleep apnea machine including said machine'components between use on patients, wherein said sleep apnea machine's components includes a sleep apnea machine reservoir, sleep apnea machine tubing, sleep apnea machine breathing mask, and sleep apnea machine air filter comprising the steps of:

a) preparing an aqueous solution comprising 5-35% by volume of alcohol, 10-50% by volume of glycerin, 0.06-2% by volume of chlorhexidine gluconate, dye and flavoring agent;

b) purging and removing water from said sleep apnea machine and said machine components;

c) introducing the aqueous solution of step a) into said sleep apnea machine and said machine components;

d) purging and removing said aqueous solution and contaminants from said sleep apnea machine and said machine's components;

e) introducing water into said sleep apnea machine and said machine components for flushing and rinsing said machine and said machine components.

* * * * *